US008574920B2

(12) United States Patent
Caron et al.

(10) Patent No.: US 8,574,920 B2
(45) Date of Patent: Nov. 5, 2013

(54) OPTICAL FIBER POLARIMETRIC CHEMICAL SENSOR WITH MODULATED INJECTION OF SAMPLE FLUID

(75) Inventors: Serge Caron, Saint-Augustin-de-Desmaures (CA); Claude Pare, Saint-Augustin-de-Desmaures (CA)

(73) Assignee: Institut National d'Optique, Quebec (CA)

( * ) Notice: Subject to any disclaimer, the term of this patent is extended or adjusted under 35 U.S.C. 154(b) by 24 days.

(21) Appl. No.: 13/182,974

(22) Filed: Jul. 14, 2011

(65) Prior Publication Data
US 2013/0014559 A1    Jan. 17, 2013

(51) Int. Cl.
*G01N 21/00* (2006.01)
*G01N 30/02* (2006.01)
*G02B 6/00* (2006.01)
*G01N 7/00* (2006.01)

(52) U.S. Cl.
USPC ........ 436/164; 436/167; 436/172; 422/82.05; 422/82.06; 422/82.07; 422/82.08; 422/82.09; 422/82.11; 422/83; 422/88; 73/23.35; 73/23.4; 385/12; 385/123

(58) Field of Classification Search
None
See application file for complete search history.

(56) References Cited

U.S. PATENT DOCUMENTS 7,403,673 B2    7/2008    Caron et al.

OTHER PUBLICATIONS

W.P. Risk, R.C. Youngquist, G.S. Kino and H.J. Shaw, Acousto-Optic Frequency Shifting in Birefringent Fiber, Optic Letters, Jul. 1984, vol. 9, No. 7, p. 309-311, Optical Society of America.
R.C. Youngquist, J.L. Brooks and H.J. Shaw, Birefringent-Fiber Polarization Coupler, Optic Letters, Dec. 1983, vol. 8, No. 12, p. 656-658, Optical Society of America.
Tal M. Nahir and Kathryn M. Morales, Constant Holdup Times in Gas Chromatography by Programming of Column Temperature and Inlet Pressure, Analytical Chemistry, Oct. 1, 2000, vol. 72, No. 19, p. 4667-4670, ACS Publications.

*Primary Examiner* — Neil N Turk
(74) *Attorney, Agent, or Firm* — Norton Rose Fulbright Canada LLP; Alexandre Daoust

(57) ABSTRACT

An optical fiber polarimetric chemical sensor for capillary gas chromatography in which a sample fluid is injected into a capillary in the form of a periodic pulse train. Each individual pulse defines a moving polarization coupling zone that affects the polarization state of the light propagating in a birefringent optical waveguide that includes the capillary. The spacing between consecutive coupling zones can be made equal to the polarization beat length of the waveguide when the injection frequency of the pulses is properly selected, thus defining a resonance condition for a given analyte. The contributions of the successive coupling zones present along the length of the capillary then add up in phase, thus resulting in a detected optical signal having an enhanced amplitude peak at the injection frequency. In this manner, the sensitivity can be enhanced.

19 Claims, 6 Drawing Sheets

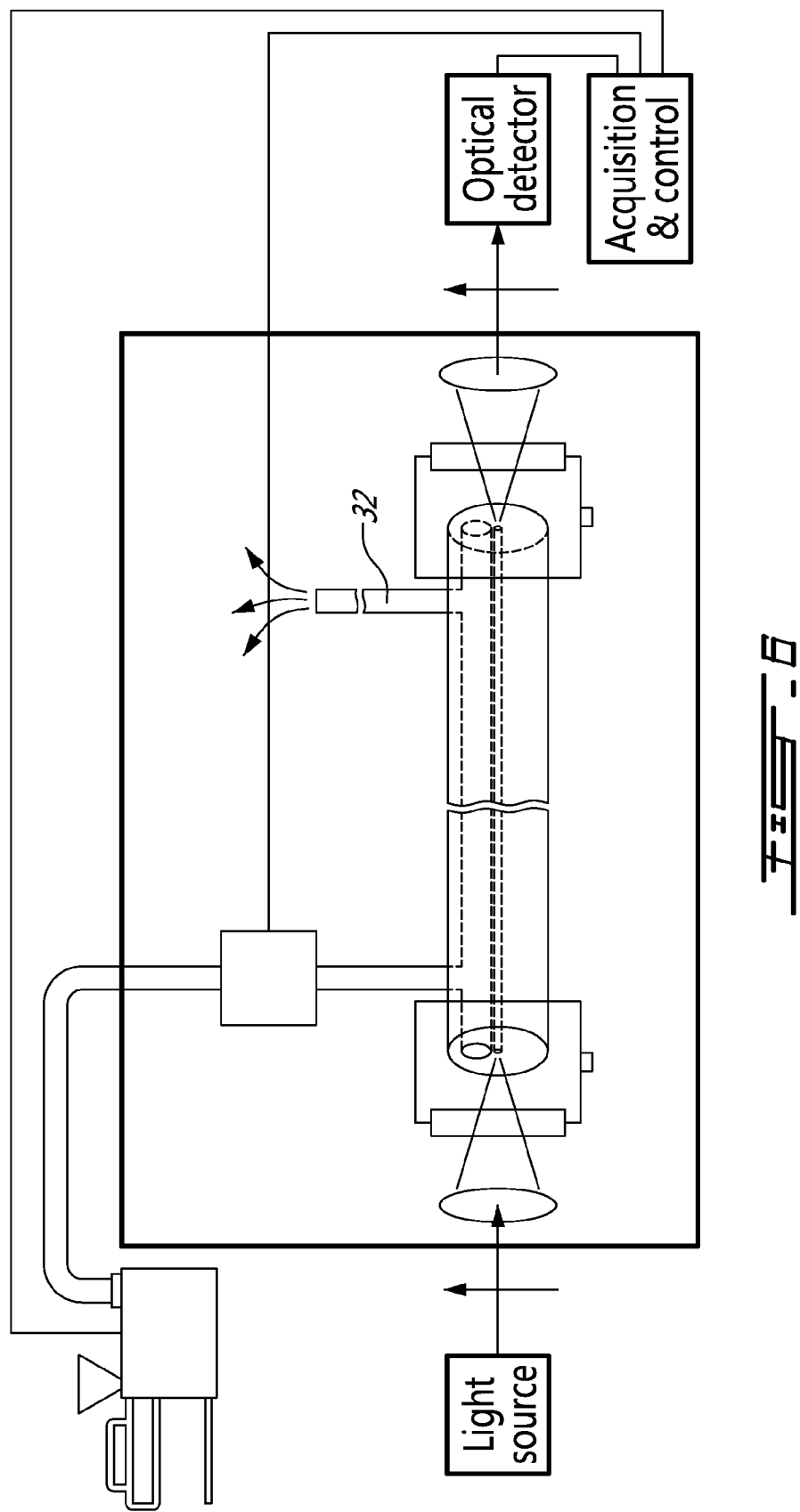

OPTICAL FIBER POLARIMETRIC CHEMICAL SENSOR WITH MODULATED INJECTION OF SAMPLE FLUID

FIELD

This application relates to optical waveguide sensors, and more particularly to optical fiber polarimetric sensors for chemical analysis based on capillary gas chromatography.

BACKGROUND

The traditional methods for capillary gas chromatography involve injecting a sample for analysis into a carrier gas. The sample is carried by the carrier gas along a capillary having an inner wall onto which the sample is partitioned, leading to a slower migration of the analyte vapors relative to the carrier gas. The partitioning involves a portion of the sample (which can be referred to as the partitioned portion) that bonds to the capillary and that is then released in a continuous process on the molecular scale. In the case where the capillary is coated with a fluid film, which is more common, the bonding occurs by absorption in the fluid film. Alternatively, the bonding can take place by adsorption on a solid surface.

The migration rate (v) of a given analyte and the flow rate (u) of the carrier gas are related by: v=pu, where p is the retention ratio. p is the probability of an analyte to be in the carrier gas (1−p being the probability of absorption). The retention ratio typically varies with the nature of the analyte, so that each analyte has a characteristic migration rate in a given sample. To facilitate understanding, reference is made to FIGS. 1A and 1B which schematically illustrate the concentrations of two different analytes migrating along the length of a capillary at two different moments.

Each analyte can thus be thought of as travelling in the form of a distinct packet, or zone of higher concentration, having a characteristic migration rate. Typically, each packet has a sharp zone distribution at the inlet of the capillary, and this zone gradually broadens as the packet travels along the capillary. The zones associated to different analytes also become progressively more spaced due to the characteristic migration rates of the analytes, which then make them more distinct.

A change in the response of a suitable sensor (such as a thermal conductivity sensor, for instance) placed at the exit of the capillary can indicate the passage of an analyte. The characteristics of the capillary and the flow rate of the carrier gas being known, a detection at a given moment can be associated with a migration rate characteristic of a specific analyte.

U.S. Pat. No. 7,403,673, the contents of which being incorporated herein by reference, teaches a new approach to chemical sensors. This approach involves guiding light in a birefringent optical waveguide that has a light propagation volume (such as a core) positioned adjacent to a capillary. The propagation volume and the capillary are close enough so that an analyte absorbed in the stationary phase can interact with the evanescent field of the guided light by altering the polarization state of the light. Information on the fluid to analyze is obtained from the detected variations in the polarization state of the light by measuring the light power transmitted through an optical polarizer placed at the output of the waveguide. This approach involves using a birefringent optical waveguide that has two different refractive indexes defining the birefringence B and the polarization beat length $L_b$. For a given light wavelength $\lambda$, both parameters are related by:

$$L_b = \frac{\lambda}{B}.$$

The beat length $L_b$ is the distance along the birefringent optical waveguide that corresponds to a phase shift of $2\pi$ between the two polarization modes of the light, and it is thus the length along the waveguide for which a polarization state of the light is recovered.

In the case of an optical fiber polarimetric chemical sensor where, for instance, linearly-polarized light is injected with its polarization direction parallel to one of the polarization axes of the optical waveguide, the presence of locally absorbed vapor in the capillary, which is adjacent to the propagation volume, transfers some of the light to the other polarization axis, and can thus be said to constitute a coupling point between the polarization axes. The new polarization state, which can be elliptical for instance, then evolves towards the optical fiber output where it can be analyzed with a polarizer. When a single light wavelength is used, as analytes are moving at speed (migration rate) v and as polarization states reproduce themselves at each distance equal to the beat length $L_b$, the light power transmitted through an output polarizer will oscillate at an oscillation frequency, or beat frequency $f_b$ given by:

$$\frac{v}{L_b}.$$

The transmittance of the optical waveguide, including the output polarizer, can be given with a good approximation by:

$$\frac{I(t)}{I_0} = \frac{1}{2} - \sum_{j=1}^{N} \kappa_j \cos\left(\frac{2\pi}{L_b} v_j + \varphi_j\right)$$

where $\phi$ is a phase term that can be discarded. The summation is performed over the analytes present in the sample fluid. The Fourier transform of the detected signal I(t) shows spectral peaks having locations that correspond to the specific migration rates of the analytes.

In the above equation $\kappa_j$ is the strength of the polarization mode coupling caused by the presence of the analyte j. This parameter is related to the concentration of each analyte and to its distribution in the capillary fiber. It will be understood that for very small quantity of analytes the mode coupling can be very small, so that the amplitude of the signal detected at the oscillation frequency $f_b$ can be too weak to be detected in the Fourier spectrum of I(t).

As a result there remains room for improvements, particularly for increasing the sensitivity of such chemical sensors.

SUMMARY

The sensitivity of the former sensor is limited by the "single-pulse" nature of the injection of the sample into the carrier gas. Indeed, at any given time there is only one coupling zone per analyte along the length of the birefringent waveguide, so there is a limit to the polarization mode coupling caused by the partitioned molecules of the given molecule type via the evanescent field of the guided light when the analyte concentration is low. Henceforth, the strength of the signal to be measured, that is the amount of light that has changed its polarization, state can be limited, thus affecting the limit of detection of the sensor.

This limit of detection can be enhanced by increasing the value of κ. One way to achieve this goal is to use periodically-varying (or multiple-pulse) sample injection instead of a point (single-pulse) injection. If the variations in the injection are done at an injection frequency $f_i$ selected to be equal to the polarization oscillation frequency $f_b$, successive analyte pulses will be separated in the passage (typically a capillary) by a distance equal to the beat length, or to an integer multiple thereof. In this manner, the later analyte pulses in the passage will cause polarization couplings that will add to the amplitude of the polarization coupling caused by the earlier analyte pulses in the passage, given the beat length of the birefringent optical waveguide. The amplitude of the signal detected at the polarization oscillation frequency $f_b$ will be increased for the given analyte, thus facilitating its detection from the Fourier spectrum of the measured signal.

In accordance with one aspect, there is provided a method of analyzing a sample fluid comprising: injecting light in a propagation volume of a birefringent optical waveguide having a beat length; injecting and circulating a sample fluid along a passage located adjacent to the propagation volume, with a partitioned portion of the sample fluid interacting with an evanescent wave of the injected light, thereby affecting the polarization state of the light thereof; modulating the injection of the sample fluid over time in a manner that a plurality of zones of higher concentration of the sample along the passage are spaced one from each other by integer multiples of the beat length.

In accordance with another aspect, there is provided a chemical sensor including a birefringent optical waveguide having a beat length, a propagation volume, and a passage defined by a partitioning material, located adjacent to the propagation volume for sample fluid conveyed in the passage to interact with an evanescent wave of light propagating in the propagation volume and thereby affect the polarization state of the light, a light source for injecting light into the propagation volume, an optical detector for detecting a periodical variation of the polarization state of the light at an oscillation frequency, caused by the flow of the sample in the passage, and a modulator for injecting the sample into the passage at a concentration varying periodically with an injection frequency.

Because the use of a liquid film is more typical in the case of capillary analysis, the expression "absorbed" will be used herein as encompassing the expression "adsorbed".

Further features and combinations thereof concerning the present improvements will appear to those skilled in the art following a reading of the instant disclosure.

BRIEF DESCRIPTION OF THE DRAWINGS

In the drawings,

FIG. 6 is a schematic view of another alternative embodiment, where the acceleration effect of the carrier gas is compensated by pressure control.

DETAILED DESCRIPTION

Figure 1:
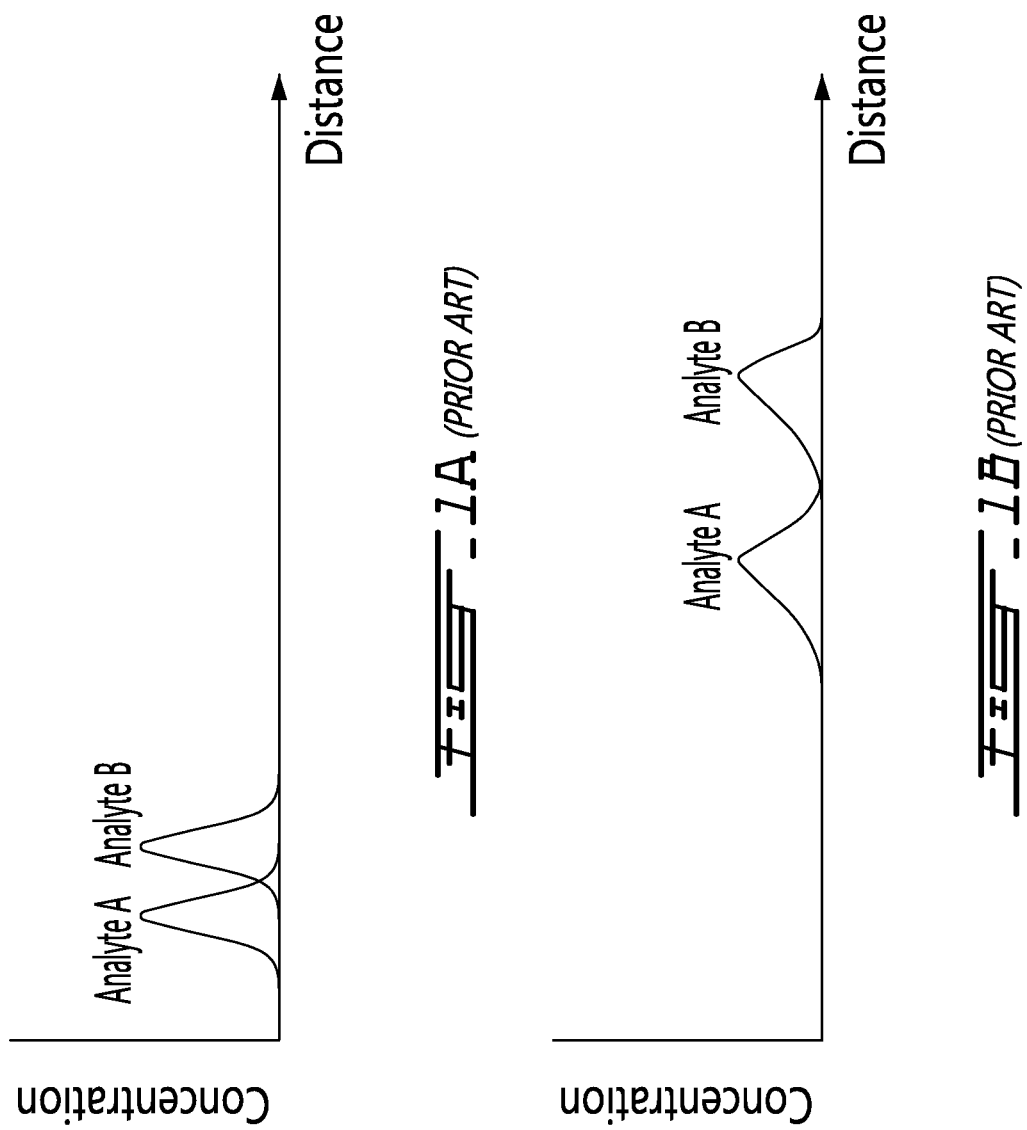
FIG. 1 is a view that illustrates the propagation of two different analytes in a capillary.

When the injection is periodical with an injection frequency $f_i$ adjusted to correspond to the oscillation frequency $f_b$ (or f(oscillation)), successive analyte pulses, or zones of higher sample concentration, can be separated from each other in the passage by a distance Λ, or pitch, being an integer multiple of the beat length (the integer multiple being one or more), in accordance with the following resonance condition:

$$\frac{1}{T(\text{injection})} = f(\text{injection}) = \frac{pu}{\Lambda} = \frac{pu}{L_b} = f(\text{oscillation}) \quad (1)$$

In other words, a first injected pulse of the sample, having a limited volume, begins to travel along the passage. The investigated analyte being present in the passage, the absorbed molecules thereof cause polarization mode coupling, i.e., a transfer of a portion of light from a first polarization mode to a second polarization mode. However, this coupling can be small since there is a limited amount of molecules of the investigated analyte in the sample. This first injected pulse travels along the passage of a birefringent optical waveguide over a given distance, and the signal being so minute, the expected mode coupling may be hardly detectable. However, a second sample pulse is injected as the first injected pulse reaches a distance equal to the beat length. This second injected pulse also causes a transfer of light to the second polarization mode, and since its injection is precisely timed, this additional signal is in phase with the signal caused by the first pulse, thus enhancing the amplitude of the detected signal. If the birefringent optical waveguide is sufficiently long, the pulses subsequently injected can all cause corresponding polarization couplings, and the detected signal at the output end of the birefringent optical waveguide will then be given by the sum of each individual timed sample pulse signal contribution, all of these contributions being in phase. Henceforth, the collective signal sum stemming from the contributions of the individual pulses present in the passage can be detected in cases where the contribution of any given individual pulse would be too weak to allow reliable detection. The sensitivity of the sensor is thus enhanced.

Injection and Diffusion

The injection can take the form of a series of pulses, each having at the entrance of the passage a concentration distribution given by $f_o(z)$. Each pulse then moves at a velocity v and diffuses, taking the form $f(z,t)$ determined by the diffusion equation (the so-called mass-balance equation). At some stage, the number of pulses present simultaneously in the passage can reach a maximum value M=L/vT, L being the fiber length, and the overall concentration distribution can read as:

$$C(z, t) = \sum_{n=0}^{M-1} f(z, t - nT) \quad (2)$$

where T is the time delay between the injection of successive pulses, that is, the reciprocal of the injection frequency.

For the sake of simplicity, we consider the specific case of a Gaussian initial pulse shape:

$$f(z, 0) = A_o \exp\left(-\frac{z^2}{W_0^2}\right). \tag{3}$$

This makes the model analytically tractable while having no impact on the main conclusions. The diffusion equation admits such a Gaussian solution. This means that each of the injected pulses maintains its Gaussian shape as it moves and diffuses along the length of the passage. The concentration distribution of the $n^{th}$ pulse spreads out and its amplitude decreases according to:

$$W_n = W_o\left[1 + \frac{4D_{eff}t_n}{W_o^2}\right]^{1/2} \tag{4}$$

and $$A_n = \frac{A_o}{\left[1 + \frac{4D_{eff}t_n}{W_o^2}\right]^{1/2}}, \tag{5}$$

where $$t_n = t - nT \tag{6}$$

corresponds to the time elapsed after the injection of the $n^{th}$ pulse. In Eqs. (4) and (5), $D_{eff}$ represents the effective diffusion coefficient of the analyte vapor. The velocity v and the effective diffusion coefficient $D_{eff}$ of any given analyte are respectively related to the velocity u and the diffusion constant D of the carrier gas through its probability of non-absorption p: v=pu and $D_{eff}$=pD.

Sensor Response

In presence of a single moving coupling zone, the capillary fiber sensor can be characterized by a periodic time variation in the light intensity I(t) transmitted through an output polarizer (and thus in the second polarization axis):

$$\frac{I(t)}{I_o} = \frac{1}{2} + \kappa \cos\left[\frac{2\pi B}{\lambda}(L - vt)\right] \tag{7}$$

with the normalized modulation amplitude κ given by $$\kappa = K\left|\int_0^L \left(\frac{dC}{dz}\right)\exp\{i\Delta\beta z\}dz\right| \tag{8}$$

where $\Delta\beta = \frac{2\pi B}{\lambda}$,

B being the fiber birefringence, K depends on the fiber design and on the properties of the stationary phase for the analyte to be detected.

It can be shown that the periodic injection of Gaussian pulses with a period T will give rise to a modulation amplitude that reads as:

$$\kappa \cong K\Delta\beta|S| \tag{9}$$

where $$S = \sqrt{\pi} \, e^{i\Delta\beta vt} A_o W_o \sum_{n=0}^{M} e^{in\Phi}\exp(-r_n^2) \tag{10}$$

with the phase delay $\Phi=\Delta\beta vT=2\pi vT/L_b$ and $r_n=\Delta\beta W_n/2=\pi W_n/L_b$, $L_b$ standing for the polarization beat length. In presence of a single pulse, the amplitude κ decays exponentially with time. The periodic injection converts this decay to a small periodic variation of period T through the time dependence of $W_n$. For our purpose, it is sufficient to evaluate the sum S at a time t corresponding to an integer multiple of the period T. The sum then becomes a geometric sum that can be evaluated analytically to yield:

$$S = \sqrt{\pi} \, e^{iM\Phi}A_o W_o \exp(-r_o^2)R \tag{11}$$

where $$r_o = \pi\frac{W_o}{L_b} \tag{12}$$

$$R = \frac{1 - \gamma^{M+1}}{1 - \gamma} \tag{13}$$

γ being defined by $$\gamma \equiv \exp\left[-\left(\frac{4\pi^2 D_{eff}T}{L_b^2} + i\Phi\right)\right] \tag{14}$$

The resonance principle that leads to an increase of the sensitivity can be expressed in mathematical form through Eqs. (11) to (14). For given injection conditions $A_o$ and $W_o$, the importance of the sensor's response depends on the injection period T, and more particularly on the phase delay $\Phi \equiv \Delta\beta vT=2\pi vT/L_b$ between each pulse contribution. In particular, |R| takes its maximum value when $\Phi=2\pi$. This corresponds to the case where the period T is chosen so as to make the pitch $\Lambda=vT$ of the analyte equal to the beat length $L_b$, hence synchronizing all of the mode coupling contributions of the pulses.

Figure 2:
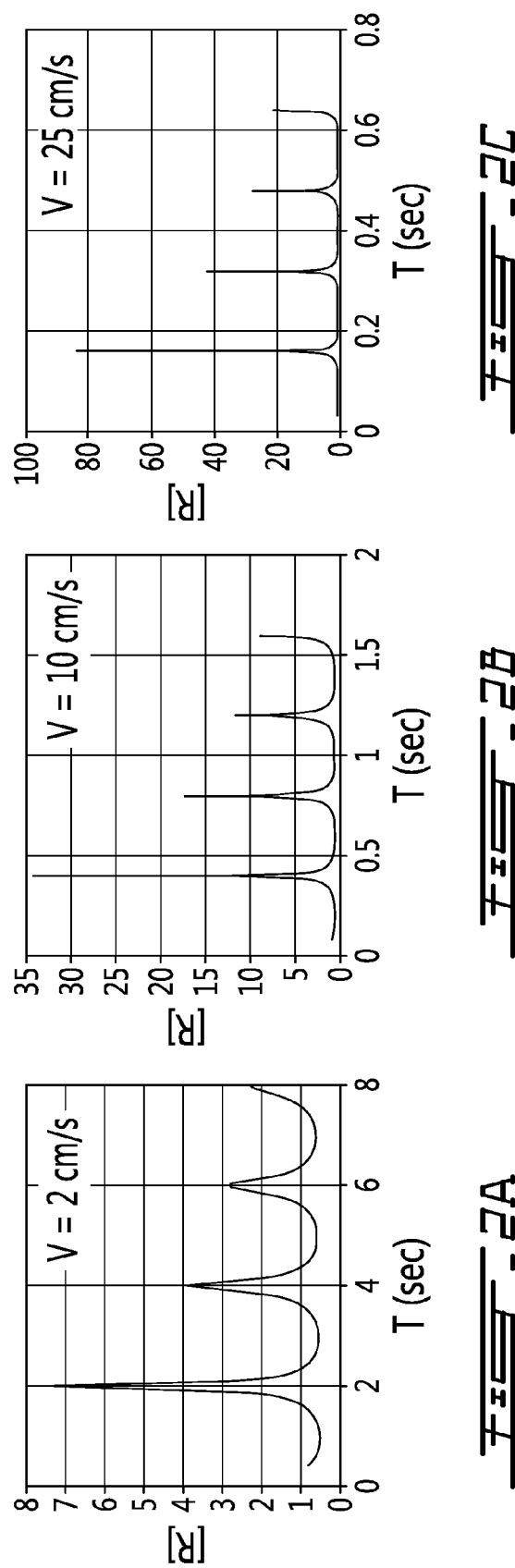
FIG. 2 is a view showing the dependence of |R| on the period, three cases are considered corresponding to three different values of the velocity of an analyte.

To better illustrate the resonance principle, FIG. 2 shows the dependence of |R| on the injection period T. Cases corresponding to three different values of the velocity v are considered. The other parameters are: L=10 m, $L_b$=4 cm and $D_{eff}$=0.03 cm²/s, and they can be considered as typical. With these values for the parameters, the injection period $T_{res}$ leading to the resonance condition is equal to 2.0 s, 0.4 s and 0.16 s, respectively.

The higher the speed of the sample fluid, the sharper the resonance curves are and so for the maximum value of |R|. This is due mostly to the decrease of the period $T_{res}=L_b/v$ leading to the resonance condition as the speed increases. This implies that each pulse has not enough time for diffusing appreciably before the next one is injected, so that the contribution of each pulse to the mode coupling is more important.

One can also notice the presence of secondary resonances. They correspond to the cases where $vT=q\, L_b$ with q= 2, 3, 4 . . . . In those cases, the number M of pulses present along the length of the fiber is lower but the main reason for the lower values of |R| is that each pulse spreads out more before the injection of the next pulse.

In practice, the fiber length and the beat length can be such that the number M of pulses is very high, so that $\gamma^{M+1} \approx 0$. Moreover, for the typically small values of the diffusion coefficient, the quantity $\gamma$ is well approximated by the first two terms of its Taylor expansion. The maximum and minimum values of R are then approximately given by:

$$R_{max} \cong \frac{vL_b}{4\pi^2 D_{eff}} = \frac{uL_b}{4\pi^2 D} \quad (15)$$

and $$R_{min} \cong \frac{1}{2} \quad (16)$$

Eq. (15) implies that the maximum gain in sensitivity does not depend on the analyte under analysis. It is primarily determined by the velocity u of the carrier gas, which can be easily modified by changing the pressure conditions.

Finally, it is worth mentioning that the dependence on the initial conditions is only through Eqs. (11) and (12) and that R does not depend on those conditions.

Figure 3:
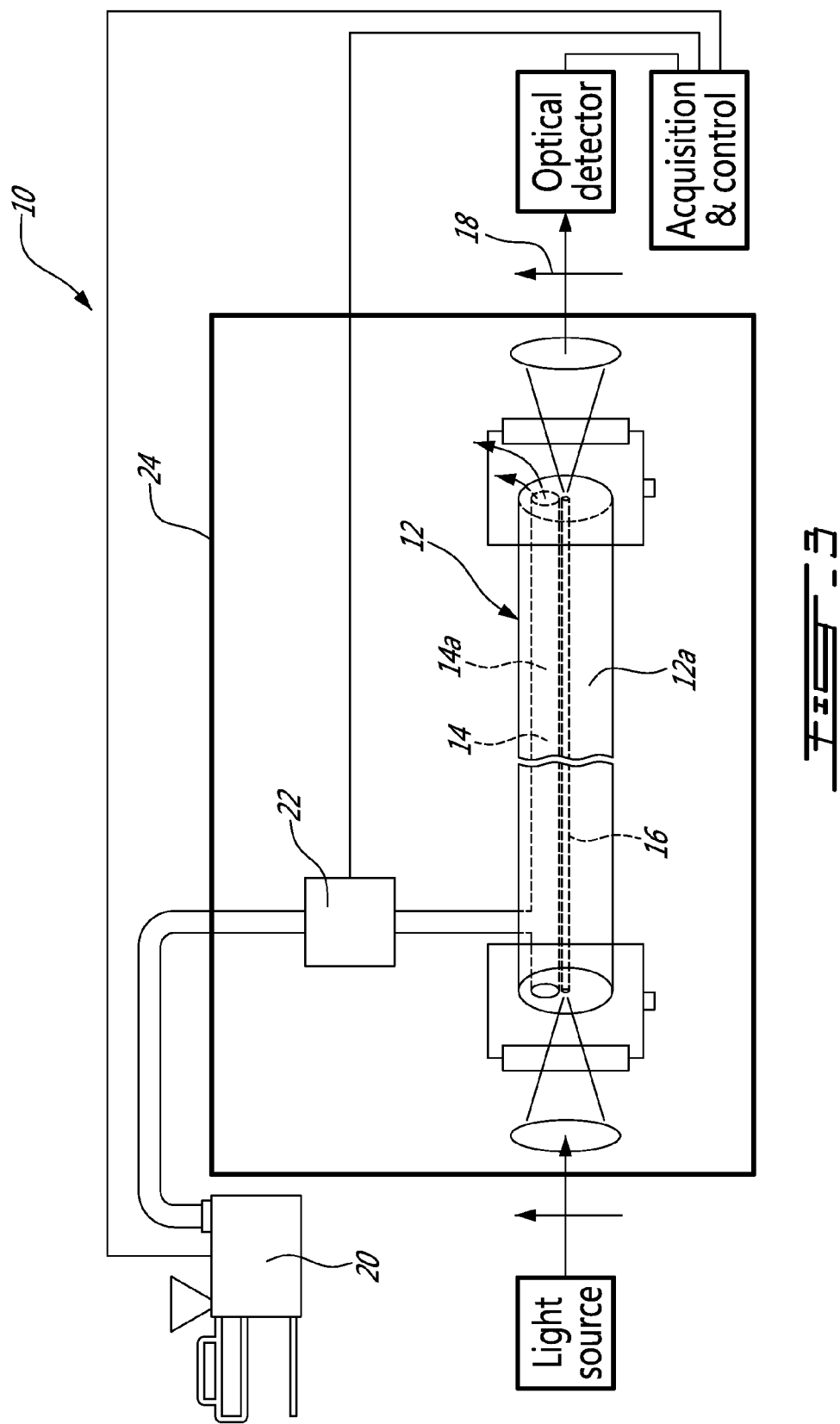
FIG. 3 is a schematic view of a first embodiment of a sensor.
Figure 4:
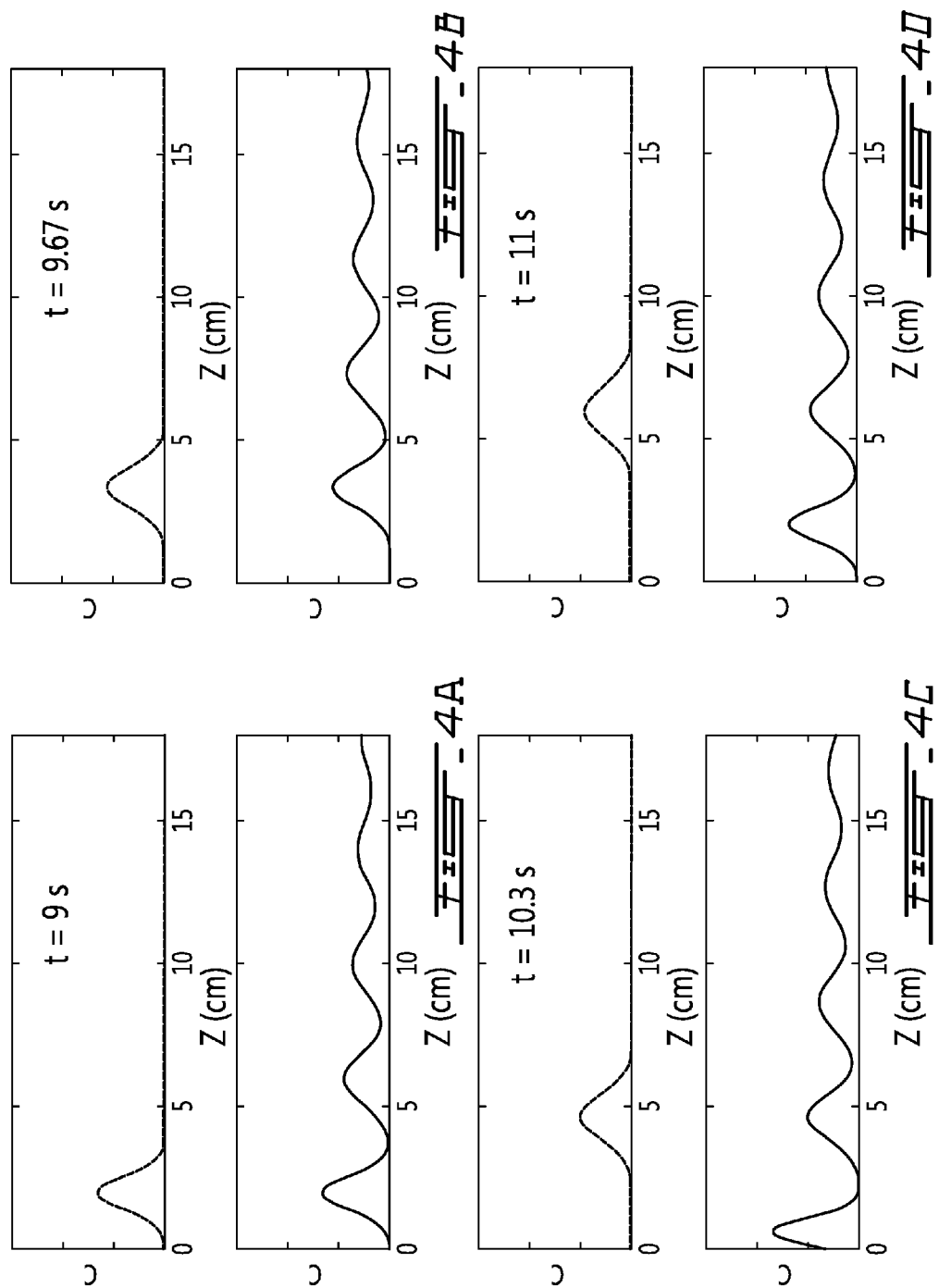
FIG. 4 shows the temporal evolution of the concentration distribution of a time-varying injection (below) compared to the temporal evolution of a single-pulse injection (above)

Referring now to FIG. 3, an example of a sensor 10 is illustrated. In this example, the optical waveguide 12 is an optical fiber 12a. The optical fiber 12a has a passage 14 for receiving the fluid to analyze. In this embodiment, the passage 14 is a capillary 14a positioned adjacent to a core 16 which acts as a propagation volume in which the light emitted from a light source 26 is guided. To favor the partition effect, the inner surface of the capillary 14a is coated with a partitioning material such as a liquid of high viscosity like polydimethylsiloxane, which is more commonly known as PDMS. In this particular embodiment, the partition effect takes place by absorption of a portion of the analytes by the partitioning material (here a film of PDMS) rather than by the inner surface of the capillary 14a. Further, in this embodiment, the light can be monochromatic, though it can alternatively be broadband, as will be detailed below. The light source 26 emits linearly-polarized light that is then injected in the core 16 of the fiber 12a. The polarization direction of the light can be parallel to either of the two polarization axes of the birefringent optical fiber 12a. Alternatively, the state of polarization of the light can be measured in order to determine any subsequent change in its polarization state that would be caused by the presence of analytes in the fluid. After travelling along the optical fiber 12a, and having interacted with the partitioned analytes via its evanescent field, the light exits from the output end of the fiber 12a. In the case of monochromatic light injected in a linearly polarized state with its direction parallel to a first polarization axis of the fiber 12a, the optical detector 28 can be positioned downstream an optical polarizer 18 having its axis oriented along the second orthogonal polarization axis of the fiber 12a. The detection of light intensity polarized parallel to the second polarization axis is thus an indication of a coupling effect caused by the interaction. The optical detector 28 can be replaced by a spectrophotometer in cases where the light source 26 emits broadband light. The power of the light emitted from the source 26 can be continuously measured in a manner to compensate for power fluctuations. In an alternative embodiment, the polarizer 18 can be replaced by a polarization beamsplitter to measure separately the power of the light polarized along each of both orthogonal polarization axes. This can also serve in compensating for power fluctuations of the light source 26 or for the optical losses in the system.

In this embodiment, the passage 14 in the optical fiber 12a is used to channel the sample fluid (gas) to analyze. The gas can be pressurized with a pump 20 to the desired pressure and then transferred to a modulator 22 that injects the gas in the passage 14 according to a periodic modulation of the concentration. The modulator 22 can, for example, use the effect of cold trapping in a capillary containing a stationary phase, or it can operate by periodical insertion of a sample vector gas in the carrier gas flux. Known devices can be used in this purpose, such as devices used in the GC×GC technique for instance. Other means of providing a varying rate of injection can be used as well.

The optical fiber 12a can be placed in an oven 24 to better control the speed of the carrier gas, particularly when an increase of the migration rates of the analytes is desired. The modulator 22 can be positioned either inside or outside of the oven 24.

The operation of the sensor 10 can be controlled by a data acquisition system 36 which can also control the modulator 22, the pump 20 (flow rate and pressure), and the optical detector 28, for instance.

In practice, the injection of satisfactorily timed distinct pulses of sample gas can be challenging, so that the injection can be modulated in a sinusoidal-like manner, for instance.

FIGS. 4A to 4D illustrate an example of such a modulation, by depicting the longitudinal distribution of an analyte concentration at different times t over one period of modulation of the injection. In each successive figure, the solid curve plotted in the lower graph shows the concentration distribution resulting from a sinusoidally-varying injection whereas the dashed curve plotted in the upper graph holds for a single pulse injection. Z represents the distance along the capillary 14a. In this example, provided for the sole purpose of illustration, the injection period is 2 s, the velocity is 2 cm/s and the effective diffusion coefficient $D_{eff}$ is 2 cm$^2$/s. FIGS. 4A to 4D progress successively from t=9 s; t=9.67 s; t=10.3 s; and t=11 s.

Typically, the injection frequency can be established as a function of a predetermined analyte for which the sensor is adapted to detect. This can be done by first determining the beat frequency for a specific analyte and test conditions, such as by testing the sensor with a sample of known analyte concentration, and then operating the sensor with a sample injection frequency set to the beat frequency before testing the presence of the analyte in actual samples.

Alternatively, or additionally to establishing the injection frequency beforehand, one can scan several injection frequencies, either by discrete steps or in continuous manner, for detecting the presence of peaks in the sensor's response associated with a given variety of molecule types. If a signal is obtained at a given injection frequency, one can then fine tune the injection frequency to attempt at strengthening the amplitude of the signal and to clearly establish the injection frequency at which a resonance is observed. Unfortunately, the scanning of the injection frequency may reveal as time consuming with some practical embodiments. Another way to look for unpredicted resonances would be to keep the injection frequency constant and then to vary the speed (u) of the carrier gas, such as by varying the pressure differential.

Another way of obtaining data is to measure the transmission spectrum of the fiber after the optical polarizer 18 for injection of broadband light. This can allow the detection of more than one analyte simultaneously. In fact, it can be noted that for multiple analytes injected at a same frequency, as the beat length depends on the wavelength of light, there will be resonances in all cases where the pitch Λ associated to an analyte equals the beat length $L_b$. A resonance peak can thus be expected in the transmitted light spectrum for each analyte present. A numerical simulation has demonstrated, for instance, that for p=0.50 and 0.52, u=85 cm/s, and Δβ=0.0256 cm$^{-1}$, resonance peaks can be expected at wavelengths of 1.297 μm and 1.349 μm, respectively. The numerical simulation also showed that the resolution was greater when the capillary 14a was longer. Accordingly, the injection can be modulated with more than one frequency.

The above description set the groundwork of the theory, but it will be noted that it was assumed up to now that the speed of the carrier gas, or the migration speed of any given analyte, would be constant along the entire length of the capillary 14a. In practice, it is likely that the speed will increase when approaching the output of the capillary due to the effect of decompression of the carrier gas.

In fact, the evolution (gradient) of the speed u of the carrier gas with the distance z along the capillary 14a is described by the following equation, as previously presented for instance in T. M. Nahir and K. M. Morales (2000) "Constant holdup times in gas chromatography by programming of column temperature and inlet pressure", Analytical Chemistry, vol. 72, pp. 4667-4670:

$$u(z) = \frac{r^2}{16L\eta} p_{in} \left(1 - \frac{p_{out}^2}{p_{in}^2}\right) \left[1 - \frac{z}{L}\left(1 - \frac{p_{out}^2}{p_{in}^2}\right)\right]^{-1/2} \quad (17)$$

where $p_{in}$ and $p_{out}$ are the inlet and outlet pressures, respectively, η is the viscosity of the gas; while L and r are the length and the radius of the capillary 14a, respectively.

Referring back to Eq. (1), it can be noted that as the gas flows through the capillary 14a, an increase of its speed u results in a corresponding increase of Λ as a function of z for a given injection frequency. Any variation of Λ with z will limit the sensitivity of the sensor 10 since it would broaden the frequency peak associated with a given analyte.

These limits can be at least partially overcome in several ways, three of which are described below.

Compensation of the Effect of Acceleration by Temperature Variation

A first way to compensate for the effect of the carrier gas acceleration is to lower the temperature (F) along the capillary 14a to increase absorption of the analytes and therefore to decrease the retention ratio p. A complete compensation for u(z) is sought, namely:

$$p(F(z)) \propto \frac{1}{u(z)} \quad (18)$$

The decompression leading to the acceleration of the carrier gas will remain present with this embodiment, but the analyte will be subjected to higher absorption as it flows through the capillary 14a. Its migration rate can remain stable by decreasing relative to the increasing carrier speed. The variations of the carrier speed as a function of temperature change can also be taken into account to achieve higher precision.

Since p will diminish when reducing F, we can expect the acceleration to be less and less important as the temperature lowers, as compared with an embodiment where the temperature would be homogeneous.

It will be noted that this type of compensation is of the first order, and it can be optimized for a specific analyte only. The variations of p with F are likely to depend on the nature of the analyte, in accordance with Arrhenius law. Nonetheless, it can be practical for monochromatic sensors adapted for the detection or quantification of a single analyte.

Figure 5:
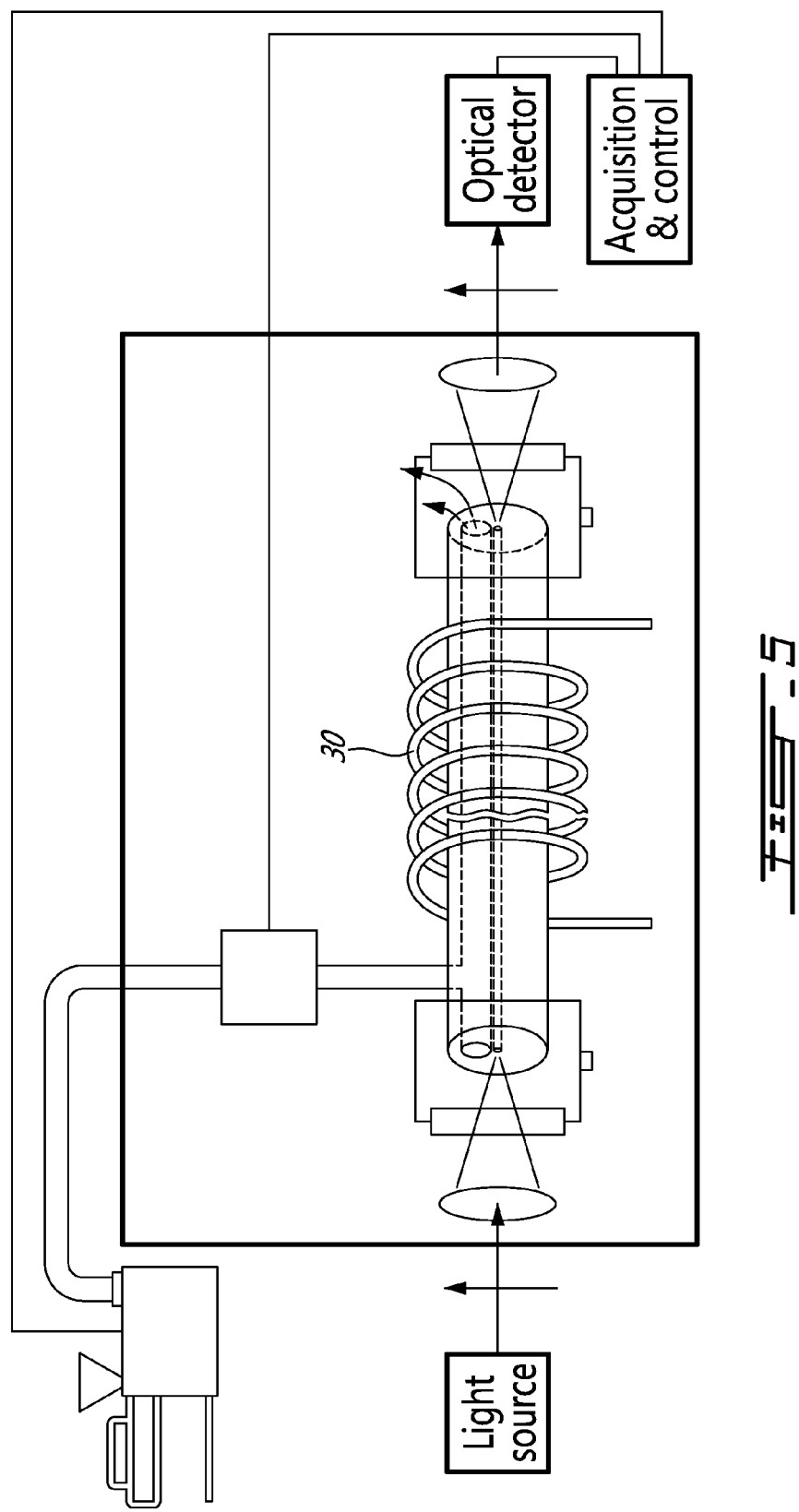
FIG. 5 is a schematic view of an alternative embodiment, where the acceleration effect of the carrier gas is compensated by a temperature gradient.

FIG. 5 shows an embodiment for compensation by temperature variation. In this embodiment, a coil 30 or another temperature control device imposes a temperature gradient along the length of the optical waveguide 12. It can be used either to reduce the temperature of the optical waveguide 12 progressively toward its exit end or to increase the temperature of the optical waveguide 12 toward its input end.

Reduction of Acceleration by Pressure Control

A way to reduce the speed gradient u(z) of the carrier gas along the capillary 14a consists in diminishing the pressure differential between the inlet and outlet of the capillary 14a and by increasing its length. In the latter case, one could connect a post column to the outlet of the capillary 14a.

By way of example, FIG. 6 illustrates an embodiment for the sensor 10 in which the outlet of the capillary 14a is connected to a column 32. Typical values for the lengths of the capillary 14a and of the post column 32 are 5 m and 16 m, respectively.

Compensation of the Effect of Acceleration by Lowering Birefringence

An additional way to compensate for the effect of the acceleration of the carrier gas is to impose a change in the birefringence of the optical fiber 12a along its length, in such a manner that the beat length $L_b$ varies with z according to the increasing pitch Λ of the analyte. The variation can be the following:

$$L_b(z) \propto u(z) \quad (19)$$

Such a variation of the fiber birefringence can be achieved in several ways. A first way would be to coil the birefringent optical fiber 12a in a spiral, such as around a conical cylinder. Alternative ways include designing the optical fiber 12a in such a manner that a variation of pressure or of temperature would have a satisfactory effect on the birefringence characteristics along its length.

Of course, two or more ways to compensate for the acceleration effect can be combined in some embodiments to get better results.

It will be understood that the embodiments shown in FIGS. 3, 5 and 6 are exemplary only, and many alternative embodiments can be realized. For instance, U.S. Pat. No. 7,403,673 illustrates different forms of birefringent waveguides that can be used to channel the sample fluid, and several optical assemblies which allow to inject both light and fluid in the optical waveguide.

The examples described above and illustrated are intended to be exemplary only. The scope is indicated by the appended claims.

What is claimed is:

1. A method of analyzing a sample fluid containing a carrier fluid and at least one analyte, said method comprising the steps of:
   (a) injecting linearly-polarized light in a propagation volume of an optical waveguide having a birefringence B, said birefringence defining a polarization beat length for any given wavelength of the injected light;
   (b) injecting the sample fluid in a passage located adjacent to the propagation volume, the passage having a partitioning material covering an inner surface of said passage and exposed to said sample fluid, said partitioning material absorbing a part of the at least one analyte contained in said flowing sample fluid, said absorbed part interacting with an evanescent wave of the light propagating in the propagation volume, thereby affecting a polarization state of the light;

(c) determining an oscillation frequency associated to a given one of the at least one analyte flowing with a characteristic migration speed over a distance corresponding to a plurality of beat lengths along the passage;

(d) modulating the injection of the sample fluid periodically at the determined oscillation frequency in a manner that a plurality of zones of higher concentration of the sample fluid is created along the passage, said zones of higher concentration being spaced from each other by an integer multiple of the beat length;

(e) detecting a presence of periodical variations in the polarization state of the light exiting from the propagation volume, the detection of said periodical variations at the determined oscillation frequency being indicative of a presence of the given one of the at least one analyte in the sample fluid.

2. The method of claim 1 further comprising
identifying a gradient of speed of the carrier fluid in the sample fluid along the passage; and
imparting a temperature gradient along the passage to cause a progressive increase in partition of the at least one analyte to compensate for the gradient of speed of the carrier fluid and to consequently reduce a corresponding gradient of speed of the at least one analyte along the passage.

3. The method of claim 1 further comprising controlling a pressure of the sample fluid at an outlet of the passage in a manner to limit a pressure differential therealong.

4. The method of claim 1 further comprising
identifying a gradient of speed of the carrier fluid in the sample fluid along the passage which causes a gradient of said spacing between said zones of higher concentration of the at least one analyte; and
imparting a gradient to the birefringence of the optical waveguide to impart a gradient in the beat length commensurate with the gradient of said spacing between said zones of higher concentration of the at least one analyte along the passage.

5. The method of claim 4 wherein said imparting is done by coiling the optical waveguide in a spiral configuration.

6. The method of claim 1 wherein the injected light is monochromatic.

7. The method of claim 1 wherein the injected light has a broad wavelength spectrum, the step (e) being done for more than one light wavelengths within the broad wavelength spectrum, the method further comprising associating a specific analyte contained in the sample fluid to each one of the at least one light wavelengths at which periodical variations of the polarization state of the light are detected.

8. The method of claim 1 wherein the injected light is linearly-polarized with a polarization direction parallel to a first polarization axis of the optical waveguide having a birefringence B, the method further comprising detecting an intensity of light exiting from the optical waveguide along a second polarization axis of the optical waveguide.

9. The method of claim 1 further comprising heating the optical waveguide.

10. A chemical sensor for analyzing a sample fluid containing a carrier fluid and at least one analyte, said sensor comprising:

a pump for pressurizing the sample fluid at a predetermined pressure;
a modulator receiving the pressurized sample fluid and varying periodically the concentration of the sample fluid according to an injection frequency, thus giving a modulated sample fluid;
a light source emitting linearly-polarized light;
an optical waveguide having a birefringence B, said birefringence defining a polarization beat length for any given wavelength of said light, said optical waveguide having:
 a propagation volume having an input end and an output end, said input end receiving said linearly-polarized light, said light propagating in said propagation volume toward said output end,
 a passage located adjacent to the propagation volume and receiving the modulated sampled fluid, the sample fluid then flowing through in the passage;
a partitioning material covering an inner surface of said passage and exposed to said flowing sample fluid, said partitioning material absorbing a part of the at least one analyte contained in said flowing sample fluid, said absorbed part interacting with an evanescent wave of the light propagating in the propagation volume and thereby affecting a polarization state of the light;
an optical polarizer receiving light from the output end of said propagation volume, said optical polarizer transmitting a part of the received light that is polarized parallel to a predetermined direction, and
an optical detector receiving light from said optical polarizer, said optical detector detecting periodical variations of the polarization state of the light at an oscillation frequency, said variations being caused by the sample fluid flowing through the passage and containing at least one analyte.

11. The chemical sensor of claim 10 wherein the modulator has a function to scan the injection frequency in at least one of by discrete steps or in continuous manner.

12. The chemical sensor of claim 10 wherein the optical waveguide is an optical fiber, the passage is a capillary and the propagation volume is a core of the optical fiber.

13. The chemical sensor of claim 10 wherein the light source emits linearly-polarized light having a polarization direction parallel to a first polarization axis of the optical waveguide and the optical detector detects part of the light that is polarized parallel to a second polarization axis of the optical waveguide.

14. The chemical sensor of claim 10 further comprising a temperature control device for imparting a temperature gradient along a length of the optical waveguide.

15. The chemical sensor of claim 10 further comprising means to reduce a pressure differential between an inlet and an outlet of the passage.

16. The chemical sensor of claim 10 wherein the optical waveguide is coiled in a spiral configuration.

17. The method of claim 1 further comprising repeating steps (c) to (e) for each of the at least one analyte present in the sample fluid.

18. The method of claim 1 further comprising the step (f) of measuring an amplitude of the detected periodical variations to obtain a relative concentration of the given one of the at least one analyte detected in the sample fluid.

19. The chemical sensor of claim 10 wherein the partitioning material is made of polydimethylsiloxane.

* * * * *